(12) United States Patent
Clausen et al.

(10) Patent No.: US 6,642,522 B2
(45) Date of Patent: Nov. 4, 2003

(54) OPTICAL GAS SENSOR

(75) Inventors: Christoph Clausen, Lübeck (DE); Wilfried Diekmann, Lübeck (DE); Günter Wahlbrink, Rehhorst (DE)

(73) Assignee: Drager Safety AG & Co. KGaA, Lübeck (DE)

( * ) Notice: Subject to any disclaimer, the term of this patent is extended or adjusted under 35 U.S.C. 154(b) by 206 days.

(21) Appl. No.: 09/941,811

(22) Filed: Aug. 29, 2001

(65) Prior Publication Data
US 2002/0063216 A1 May 30, 2002

(30) Foreign Application Priority Data
Nov. 24, 2000 (DE) .......................... 100 58 469

(51) Int. Cl.$^7$ .............................. G01N 21/61
(52) U.S. Cl. ................. 250/343; 250/339.13; 250/373; 356/437; 356/440
(58) Field of Search ................. 250/343, 339.04, 250/339.13, 353, 341.8, 373; 356/437, 439, 440

(56) References Cited

U.S. PATENT DOCUMENTS 3,997,786 A * 12/1976 Lauer et al. ............. 250/343
4,228,352 A * 10/1980 Adrian .................... 250/343
5,163,332 A * 11/1992 Wong ................... 73/863.23
5,696,379 A * 12/1997 Stock ..................... 250/343
5,973,326 A   10/1999 Parry et al.
6,313,464 B1 * 11/2001 Schrader ................ 250/349
6,469,303 B1 * 10/2002 Sun et al. ............... 250/343

FOREIGN PATENT DOCUMENTS

DE        195 20 488 C1    9/1996

* cited by examiner

Primary Examiner—Albert Gagliardi
(74) Attorney, Agent, or Firm—McGlew and Tuttle, P.C.

(57) ABSTRACT

An optical gas sensor has a compact design and without movable optical elements, with at least one radiation source (8), at least one measuring detector (9, 12) and a reference detector (11). The reflecting measuring cuvette is designed as an annular space (1) between a first, inner cylinder section (6) and a second, outer cylinder section (2) that is concentric thereto. The annular space (1) is limited by a cover element (5) and a bottom element (7) arranged at a spaced location therefrom in the direction of the longitudinal axis. The cover element (5) is permeable to the measuring gas. The bottom element (7) accommodates the radiation source (8).

13 Claims, 2 Drawing Sheets

OPTICAL GAS SENSOR

FIELD OF THE INVENTION

The present invention pertains to an optical gas sensor with at least one radiation source, with a reference detector and with at least one measuring detector in a reflecting measuring gas cuvette.

BACKGROUND OF THE INVENTION

Compact gas analyzers can make possible low manufacturing costs and a robust design because no movable optical components are used. These may be made available with such gas sensors, as disclosed, e.g., in DE 195 20 488 C1 and in U.S. Pat. No. 5,973,326, which form this gas analyzer type.

The known principle of measurement of the gas sensors of this type is based on the concentration-dependent absorption of electromagnetic radiation especially in the infrared wavelength range by the gas to be measured, the measuring gas. The measuring gas, e.g., hydrocarbons, $CO_2$ and other trace gases, diffuses, in general, through a dust protection membrane or a flame arrester in the form of a fabric or a gas-permeable layer of a sintered or ceramic material into the cuvette volume of the measuring gas cuvette of the gas sensor.

The radiation of at least one broad-band radiation source covering, in general, a rather broad wavelength range passes through the measuring gas cuvette. An incandescent lamp or an electrically heated glass or ceramic element is usually used as the radiation source. The radiation emitted divergently from the electromagnetic radiation source, of which there is at least one, is bundled by means of optically reflecting surfaces in order to increase the radiation intensity at the site of the measuring and reference detectors. The signal-to-noise ratio of the gas sensor is increased by the bundling of the radiation and the quality of the measurement is thus improved. The detectors used are, in general, pyroelectric crystals, semiconductor elements or so-called thermoelectric piles formed of thermocouples. These different types of detectors convert radiation power into electric signals. The signals are evaluated in a suitable manner for the determination of the gas concentration to be measured. If two or more different measuring gases are to be measured with one gas sensor, a number of measuring detectors, whose number corresponds to the number of the different measuring gases, are used, which are sensitive to a particular measuring gas in a wavelength-specific manner. The wavelength range or wavelength ranges is/are selected by means of interference filters, which are connected, in general, directly to the corresponding detectors or are combined with same. A first wavelength range contains the wavelength of an absorption band of the measuring gas and is detected by the corresponding measuring detector, while the second wavelength range detected by the reference detector is selected such that it is not affected by the absorption of the measuring gas. The concentration of the measuring gas is determined and the influence of aging effects of the radiation source as well as the effect of possible contaminations in the optical beam path are compensated by forming the quotient and by suitably taking into account the measured signals.

SUMMARY AND OBJECTS OF THE INVENTION

The object of the present invention is to provide a gas sensor of this type, which makes possible a very compact design with improved measuring sensitivity.

According to the invention, an optical gas sensor is provided with at least one radiation source, with a reference detector and with at least one measuring detector in a reflecting measuring gas cuvette. The measuring gas cuvette has a first inner cylinder section and a second outer cylinder section defining an annular space therebetween. The first inner cylinder section and the second outer cylinder section are preferably concentric. The annular space is limited by a cover element and a bottom element arranged at a spaced location therefrom in the direction of a longitudinal axis. The cover element is permeable to the measuring gas. The bottom element accommodates the radiation source.

The measuring detector, of which there is at least one, and/or the reference detector may be arranged in the bottom element. The cover element and the bottom element may extend essentially in parallel to one another and at right angles to the central longitudinal axis of the cylinder sections. A temperature sensor may be arranged in the first, inner cylinder section.

The radiation source and one of the measuring detectors are arranged in opposite sections of the annular space.

The radiation source and the measuring detector may be arranged at closely spaced locations next to one another with a reflecting wall blocking the annular space in the circumferential direction, so that direct beam paths from the radiation source to the measuring detector are blocked in the circumferential direction in the annular space and the radiation travels circumferentially opposite the direct path around the first, inner cylinder section.

One important advantage of the gas sensor according to the present invention is the rotationally symmetrical design of the measuring gas cuvette as an annular space, as a result of which the beam path or beam paths between the radiation source or radiation sources and the detectors is made longer, on average, because of multiple reflections, and as a result of which simple manufacture without complicated adjustments is also possible.

Furthermore, it is advantageous that the gas-carrying volume is reduced by the first, inner cylinder section, so that a shorter response time of the gas sensor according to the present invention is obtained as a result.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
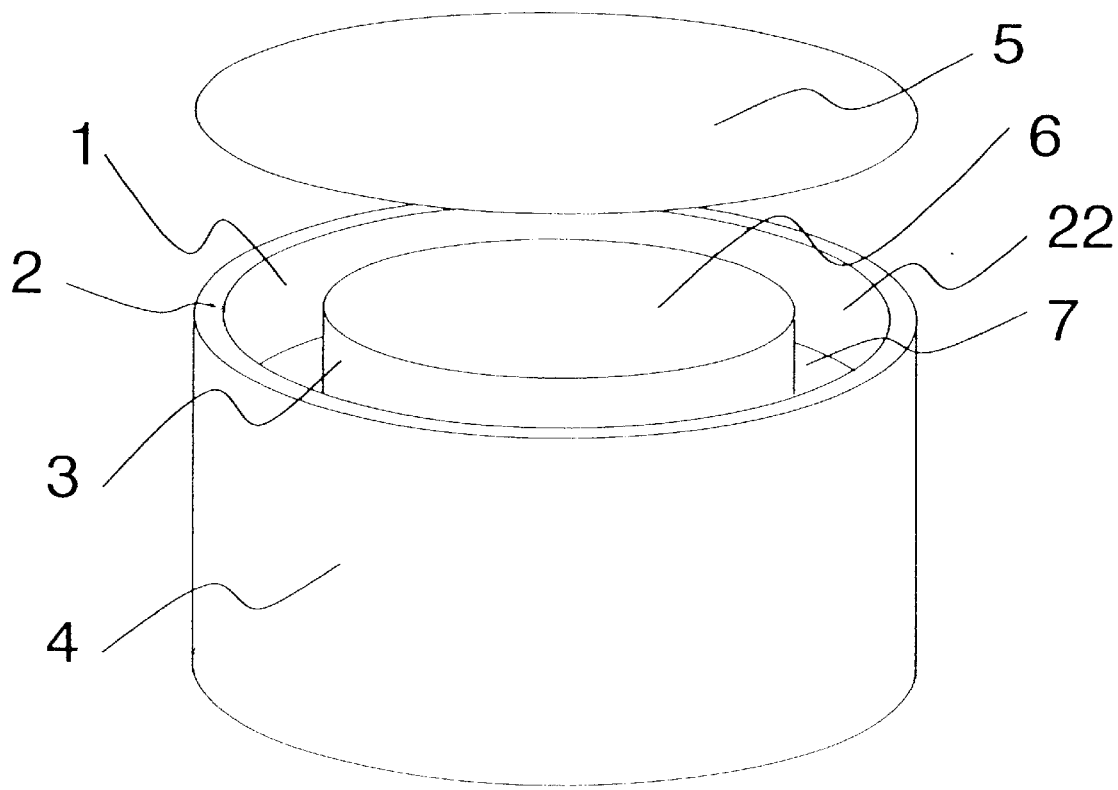
FIG. 1 shows a view of the gas sensor according to the present invention with the cover element 5 lifted off.
Figure 2:
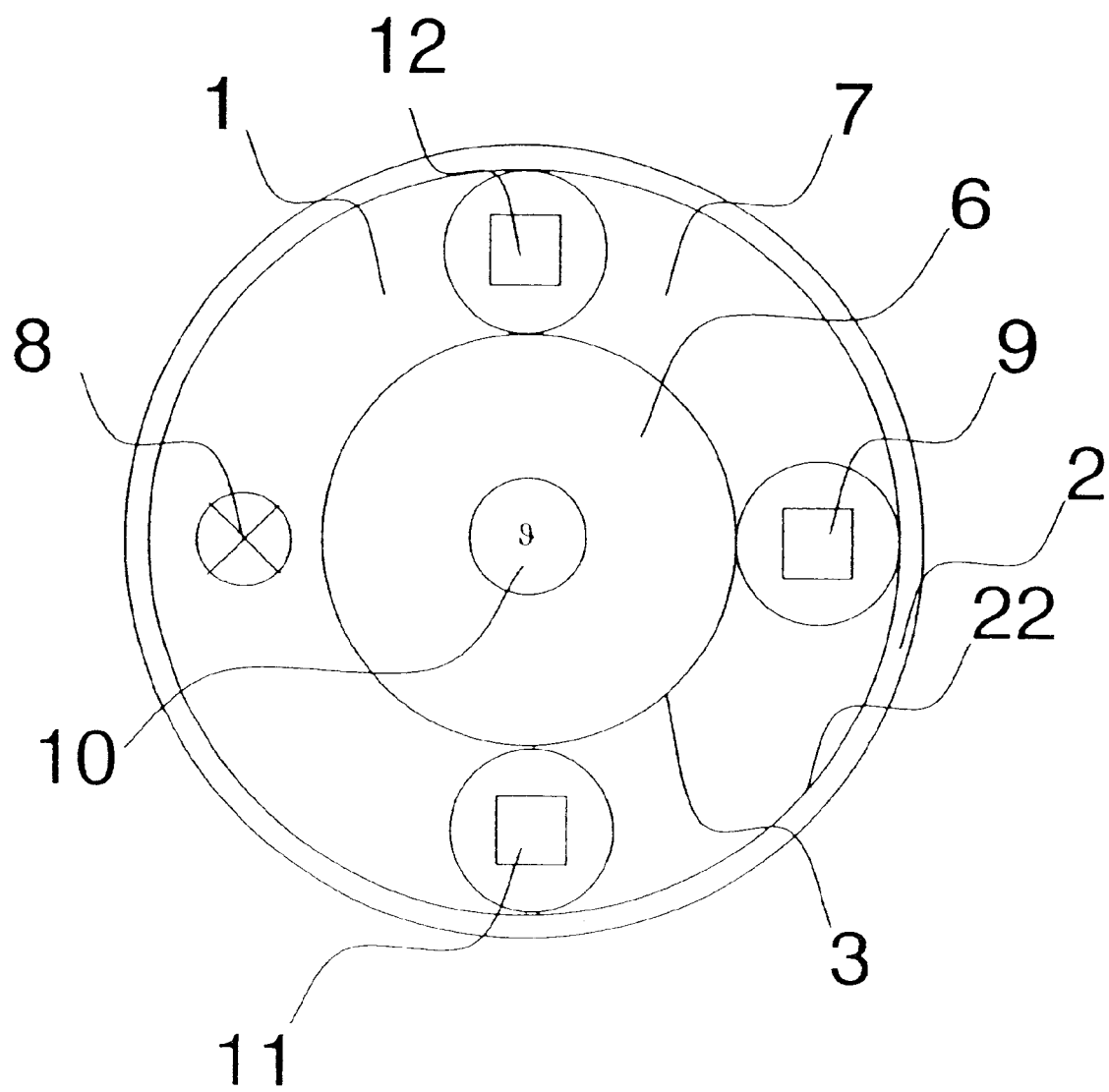
FIG. 2 shows a cross section through the gas sensor with view toward the bottom element 7.

Referring to the drawings in particular, the present invention makes do without individual precision optical components, especially movable optical components, in order to provide a robust, compact and inexpensive optical gas sensor, which is arranged in a sensor housing 4.

The radiation source 8, which is the only radiation source in the example, is a known broad-band radiation source with an associated reference detector 11 and with a first measuring detector 9 for a first measuring gas and with a second measuring detector 12 for a second measuring gas, as well as optionally with additional measuring detectors for additional measuring gases. The use of a plurality of radiation sources 8, arranged at different distances from the measuring detector or measuring detectors, especially with different modulation frequencies, is also possible according to the invention.

The beam paths from the radiation source 8 to the detectors are located within the measuring gas cuvette, which is designed as an annular space 1 and whose walls are designed as reflecting walls and are made especially from metallic materials.

The annular space 1 is limited by a first, inner cylinder section 6 with a reflecting wall surface 3, which is an inner wall surface relative to the annular space 1, and with a reflecting wall surface 22, which is an outer wall surface relative to the annular space 1, as well as by a reflecting cover element 5, which is an upper cover element in FIG. 1, and a lower reflecting bottom element 7, which extend essentially in parallel to one another and at right angles to the central longitudinal axis of the cylinder sections 2, 6. Generally long beam paths are obtained in the reflecting measuring gas cuvette designed as an annular space 1 and used as a light guide due to the circular ring-shaped design. In particular, the propagation of the light takes place as a result due to multiple reflections between the cover element 5, the bottom element 7, the first, inner cylinder section 6, and the second, outer cylinder section 2, which is advantageously concentric or substantially concentric to the first cylinder section 6.

In a special embodiment with good signal-to-noise ratio, the radiation source 8 and the first measuring detector 9 are positioned at 180° in relation to one another in relation to the cylinder sections 2, 6, i.e., in opposite sections of the annular space 1, and the reference detector 11 is positioned at an angular distance in the range of up to 90° in relation to the first measuring detector 9. The reference detector 11 is preferably located as close to the first measuring detector 9 as possible in order to receive possibly equal radiation intensities for good evaluation. A special embodiment of this special design was built for the determination of the concentration of methane with a corresponding characteristic measuring wavelength, where the diameter of the second, outer cylinder section 2 was about 18 mm and that of the first, inner cylinder section 6 was about 12 mm, and the depth or height of the annular space 1 was about 13 mm.

The use of a multiple detector, which combines the functions of both the measuring detector or measuring detectors and the reference detector with corresponding interference filters in one compact set-up, is optimal.

A temperature sensor 10, which is designed, e.g., as a semiconductor element, is arranged in the first, inner cylinder section 6, so that changes in temperature due to changes in the ambient conditions are detected and taken into account in the evaluation and the compensation of the detector signals.

Depending on the number of the measuring detectors used for the different gases to be measured, they can be positioned corresponding to the beam path in the annular space 1 depending on the design of the desired absorption section. For example, the measurement of hydrocarbons requires, in general, a longer absorption section corresponding to a longer beam path than the measurement of carbon dioxide.

In another special embodiment of the present invention, the radiation source 8 and one or more measuring detectors are arranged at closely spaced locations next to one another, but the direct beam path from the radiation source 8 to the measuring detector or measuring detectors is excluded by a reflecting wall between the radiation source 8 and the measuring detector or measuring detectors, the wall blocking the annular space 1 for direct beam paths in the circumferential direction, so that the radiation travels over the longer path around the first, inner cylinder section 6 and opposite the direct path.

In another special embodiment, the cover element 5, which reflects into the interior of the gas sensor and is permeable to the measuring gas or measuring gases, is made non-reflecting in selected surface areas. The consequence of this is that absorption sections and consequently beam paths that are too short and therefore do not contribute to the improvement of the signal can be excluded, so that the measuring sensitivity of the gas sensor is thus improved. The selected surface areas of the cover element 5 may be prepared, e.g., by blackening the generally metallic or metallized surface or by enlarging the openings intended for the entry of the measuring gas or measuring gases.

The electric components radiation source 8 and detectors are preferably located opposite the side of the sensor intended for the entry of the gas, i.e., in or at the bottom element 7, so that the signals can be sent together in a space-saving and simple manner, e.g., for evaluation in a portable, compact gas-measuring device.

While specific embodiments of the invention have been shown and described in detail to illustrate the application of the principles of the invention, it will be understood that the invention may be embodied otherwise without departing from such principles.

What is claimed is:

1. An optical gas sensor, comprising:
    a first inner cylinder section;
    a second outer cylinder section, said first inner cylinder section being substantially concentric to said second outer cylinder;
    a cover element permeable to the measuring gas;
    a bottom element arranged at a spaced location from said cover element in the direction of a longitudinal axis of said first inner cylinder section and said second outer cylinder section with said first inner cylinder section, said second outer cylinder section, said cover element and said bottom element having reflective surfaces and forming an annular space of a reflecting gas cuvette;
    at least one radiation source, said bottom element accommodating said radiation source;
    a reference detector in said annular space; and
    a measuring detector in said annular space.

2. An optical gas sensor in accordance with claim 1, wherein at least one of the measuring detector and the reference detector is arranged in the bottom element.

3. An optical gas sensor in accordance with claim 1, wherein said cover element and said bottom element extend substantially in parallel to one another and substantially at right angles to said longitudinal axis.

4. An optical gas sensor in accordance with claim 1, wherein a temperature sensor is arranged in said first inner cylinder section.

5. An optical gas sensor in accordance with claim 1, wherein said radiation source and one of said measuring detector and said reference detector are arranged in opposite sections of said annular space.

6. An optical gas sensor in accordance with claim 1, wherein said radiation source and said measuring detector are arranged at closely spaced locations next to one another with a reflecting wall blocking the annular space in a circumferential direction whereby direct beam paths from said radiation source to said measuring detector are blocked in said circumferential direction in said annular space and said radiation travels circumferentially opposite to said direct path around said first inner cylinder section.

7. A method for gas sensing, comprising:

providing a first inner cylinder section;

providing a second outer cylinder section;

providing a cover element permeable to the measuring gas;

providing a bottom element;

arranging the first inner cylinder section concentrically or substantially concentrically to the second outer cylinder with the bottom element spaced from the cover element in the direction of a longitudinal axis of the first inner cylinder section and the second outer cylinder section with the first inner cylinder section, second outer cylinder section, the cover element and the bottom element having reflective surfaces and forming an annular space of a reflecting gas cuvette;

providing at least one radiation source accommodated in the annular space;

providing a reference detector in the annular space;

providing a measuring detector in the annular space; and sensing gas by directing radiation from the radiation source through the annular space using the reflective surfaces to the measuring detector and reference detector.

8. A method in accordance with claim 7, wherein at least one of the measuring detector and the reference detector is arranged in the bottom element.

9. A method in accordance with claim 7, wherein the cover element and the bottom element extend substantially in parallel to one another and substantially at right angles to the longitudinal axis.

10. A method in accordance with claim 7, wherein a temperature sensor is arranged in the first inner cylinder section.

11. A method in accordance with claim 7, wherein the radiation source and one of the measuring detector and the reference detector are arranged in opposite sections of the annular space.

12. A method in accordance with claim 7, wherein the radiation source and the measuring detector are arranged at closely spaced locations next to one another with a reflecting wall blocking the direct path through the annular space in a circumferential direction and further comprising the step of;

directing beam paths from the radiation source to the measuring detector such that they are blocked in the direct path in the circumferential direction in the annular space and the radiation travels circumferentially opposite to the direct path around the first inner cylinder section.

13. An optical gas sensor with a compact design and without movable optical elements, the optical gas sensor being formed by the steps comprising:

providing at least one radiation source, at least one measuring detector and a reference detector;

providing a reflecting measuring cuvette with an annular space between a first inner cylinder section and a second, outer cylinder section that is concentric thereto;

limiting the annular space by a cover element and a bottom element arranged at a spaced location therefrom in the direction of a longitudinal axis of the cylinders;

making the cover element permeable to the measuring gas; and accommodating the radiation source in the bottom element.

* * * * *